(12) United States Patent
Eichmeyer et al.

(10) Patent No.: US 7,833,707 B2
(45) Date of Patent: *Nov. 16, 2010

(54) METHODS OF OVEREXPRESSION AND RECOVERY OF PORCINE CIRCOVIRUS TYPE 2 ORF2

(75) Inventors: Marc Eichmeyer, Bondurant, IA (US); Greg Nitzel, Mattawan, MI (US); Merrill Schaeffer, St. Joseph, MO (US)

(73) Assignee: Boehringer Ingelheim Vetmedica, Inc., Saint Joseph, MO (US)

( * ) Notice: Subject to any disclaimer, the term of this patent is extended or adjusted under 35 U.S.C. 154(b) by 1315 days.

This patent is subject to a terminal disclaimer.

(21) Appl. No.: 11/034,797

(22) Filed: Jan. 13, 2005

(65) Prior Publication Data

US 2009/0042245 A1 Feb. 12, 2009

Related U.S. Application Data

(60) Provisional application No. 60/640,510, filed on Dec. 30, 2004.

(51) Int. Cl.
*C12Q 1/68* (2006.01)
(52) U.S. Cl. ........................................................ 435/6
(58) Field of Classification Search ................. 435/6
See application file for complete search history.

(56) References Cited

U.S. PATENT DOCUMENTS

| | | | |
|---|---|---|---|
| 5,322,774 A * | 6/1994 | Peakman et al. ........... 435/69.1 |
| 6,217,883 B1 | 4/2001 | Allan et al. |
| 6,368,601 B1 | 4/2002 | Allan et al. |
| 6,391,314 B1 | 5/2002 | Allan et al. |
| 6,497,883 B1 * | 12/2002 | Bublot et al. ............. 424/204.1 |
| 6,517,843 B1 | 2/2003 | Ellis et al. |
| 6,660,272 B2 | 12/2003 | Allan et al. |
| 6,703,023 B1 | 3/2004 | Jestin et al. |
| 7,109,025 B1 * | 9/2006 | Eloit et al. ............... 435/320.1 |
| 7,223,407 B2 * | 5/2007 | Jestin et al. .............. 424/199.1 |
| 7,407,803 B2 | 8/2008 | Jestin |
| 7,425,444 B2 | 9/2008 | Jestin |
| 7,700,285 B1 * | 4/2010 | Eichmeyer et al. ............. 435/6 |
| 2003/0170270 A1 | 9/2003 | Meng et al. |
| 2004/0062775 A1 | 4/2004 | Jestin |
| 2004/0076635 A1 | 4/2004 | Jestin |
| 2004/0091502 A1 | 5/2004 | Jestin |
| 2004/0132178 A1 | 7/2004 | Haines |
| 2004/0161410 A1 | 8/2004 | Jestin |
| 2004/0253270 A1 | 12/2004 | Meng |
| 2004/0265848 A1 | 12/2004 | Jestin |
| 2005/0008651 A1 | 1/2005 | Jestin |
| 2005/0058653 A1 | 3/2005 | Ellis |
| 2005/0079185 A1 | 4/2005 | Parisot |
| 2005/0084497 A1 | 4/2005 | Jestin |
| 2006/0002952 A1 | 1/2006 | Haines |
| 2006/0029617 A1 | 2/2006 | Charreyre |
| 2006/0115489 A1 | 6/2006 | Birkett |
| 2006/0204522 A1 | 9/2006 | Kroll |
| 2006/0222659 A1 | 10/2006 | Jestin |
| 2006/0233831 A1 | 10/2006 | Parisot |
| 2006/0286123 A1 | 12/2006 | Fetzer |
| 2007/0196879 A1 | 8/2007 | Chabriere et al. |
| 2008/0181910 A1 | 7/2008 | Roof |
| 2008/0233147 A1 | 9/2008 | Jestin |
| 2008/0261887 A1 | 10/2008 | Roof |
| 2008/0279875 A1 | 11/2008 | Roof |
| 2008/0279876 A1 | 11/2008 | Roof |
| 2008/0279889 A1 | 11/2008 | Roof |

FOREIGN PATENT DOCUMENTS

| | | |
|---|---|---|
| EP | 1281760 A1 | 2/2003 |
| EP | 1386617 A1 | 2/2004 |
| WO | 89/06972 A1 | 8/1989 |
| WO | 90/07935 A1 | 7/1990 |
| WO | 91/18627 A1 | 12/1991 |
| WO | 92/03157 A1 | 3/1992 |
| WO | 93/16726 A2 | 9/1993 |
| WO | 95/30437 A1 | 11/1995 |
| WO | 99/18214 A1 | 4/1999 |
| WO | 99/29717 A3 | 6/1999 |
| WO | 99/29871 A3 | 6/1999 |
| WO | WO0047756 | 2/2000 |
| WO | WO0077188 | 12/2000 |
| WO | 01/16330 A3 | 3/2001 |
| WO | 01/17550 A2 | 3/2001 |
| WO | 01/17551 A2 | 3/2001 |
| WO | 01/17556 A1 | 3/2001 |
| WO | 02/49666 A2 | 6/2002 |
| WO | 03/003941 A2 | 1/2003 |
| WO | 2004/058142 A2 | 7/2004 |
| WO | 2004/069184 A2 | 8/2004 |
| WO | 2005/009462 A2 | 2/2005 |
| WO | 2006/072065 A2 | 7/2006 |
| WO | 2006/113372 A2 | 10/2006 |
| WO | 2006/113373 A2 | 10/2006 |
| WO | 2007/028823 A1 | 3/2007 |
| WO | 2007/076520 A2 | 7/2007 |

(Continued)

OTHER PUBLICATIONS

S Inumaru et al, Immunology and Cell Biology, 1998, vol. 76, pp. 195-201.*

(Continued)

*Primary Examiner*—Ali R. Salimi
(74) *Attorney, Agent, or Firm*—Michael P. Morris; Julie A. Scott

(57) ABSTRACT

An improved method for recovering the protein expressed by open reading frame 2 from PCV2 is provided. The method generally involves the steps of transfecting recombinant virus containing open reading frame 2 coding sequences into cells contained in growth media, causing the virus to express open reading frame 2, and recovering the expressed protein in the supernate. This recovery should take place beginning approximately 5 days after infection of the cells in order to permit sufficient quantities of recombinant protein to be expressed and secreted from the cell into the growth media. Such methods avoid costly and time consuming extraction procedures required to separate and recover the recombinant protein from within the cells.

18 Claims, 2 Drawing Sheets

OTHER PUBLICATIONS

Liu et al, Protein Express and Purification, 2001, 21:115-120.*

Kim et al, J. Veterinary Science, 2002, vol. 3, No. 1, pp. 19-23.*

Yang, Zong-zhao, A survey on porcine circovirus type 2 infection and phylogenetic analysis of its ORF2 gene in Hangzhou, Zhejiang Province, China, J Zhejiang Univ Sci B. Feb. 2008; 9(2): 148-153.

Does stress-free livestock mean safer food?, http://www.foodnavigator.com/Financial-Industry/Does-stress-free-livestock-mean-safer-food, Jun. 4, 2004.

Vaccination Guidelines For Swine, VIDO Swine Technical Group—Linking knowledge to practical solutions, Vaccination Guidelines, www.vido.org, Jun. 2004.

Liu et al., Characterization of a Previously Unidentified Viral Protein in Porcine Circovirus Type 2-Infected Cells and Its Role in Virus-Induced Apoptosis, J Virol, Jul. 2005, vol. 79, No. 13, p. 8262-8274.

Morris et al., Promoter Influence on Baculovirus-Mediated Gene Expression in Permissive and Nonpermissive Insect Cell Lines, J Virol, Dec 1992, vol. 66, No. 12, p. 7397-7405.

Morris et al., Characterization of Productive and Non-productve ACMNPV Infection in Selected Insect Cell Lines, Virol 197, 1993, 339-348.

Fan et al., Immunogenicity of Empty Capsids of Porcine Circovius Type 2 Produced in Insect Cells, Veterinary Research Communications, 2007, 31:487-496.

Reproduction of postweaning multisystemic wasting syndrome in pigs experimentally inoculated with a Swedish porcine circovirus 2 isolate; Allan, McNeilly, Meehan, McNair, Ellis, Krakowka, Fossum, Wattrang, Wallgren Adair; J Vet Diagn Invest 15:553-560(2003).

Experimental reproduction of postweaning multisystemic wasting syndrome in cesarean-derived, colostrum-deprived piglets inoculated with porcine circovirus type 2 (PCV2): investigation of quantitative PCV2 distribution and antibody responses; Okuda, Ono, Yazawa, Shibata; J Vet Diagn Invest 15:107-114 (2003).

Postweaning multisystemic wasting syndrome induced after experimental inoculation of cesarean-derived, colostrum-deprived piglets with type 2 porcine circovirus; Bolin, Stoffregen, Nayar, Hamel; J Vet Diagn Invet 13:185-194 (2001).

Clinical and pathological observations on pigs with postweaning multisystemic wasting syndrome; Quintana, Segales, Rosell, Calsamiglia, Rodriguez-Arrioja, Chianini, Folch, Maldonado, Canal, Plana-Duran, Domingo; The Veterinary Record, (2001) 149:357-361.

PCV-2 Infection in swine; more than just postweaning multisystemic wasting syndrome; Guest Editorial; The Veterinary Journal 166 (2003) 222-223.

Vaccination Ramification? An objective look at how vaccination might affect post-weaning multisystemic wasting syndrome (PMWS) and porcine dermatitis and nephropathy syndrome (PDNS); Mackinnon; The Pig Journal (2003) 51, 36-63.

Modified Indirect Porcine Circovirus (PCV) Type 2-Based and Recombinant Capsid Protein (ORF2)-Based Enzyme-Linked Immunosorbent Assays for Detection of Antibodies to PCV; Nawagitgul, Harms, Morozov, thacker, Sorden, Lekcharoensuk, Paul; Clinical and Diagnostic Laboratory Immunology, Jan. 2002, p. 33-40 (vol. 9. No. 1).

Cytokine profiles of peripheral blood mononuclear cells from pigs with postweaning multisystemic wasting syndrome in response to mitogen, superantigen or recall viral antigens; Darwich, Balasch, Plana-Duran, Segales, Domingo, Mateu; Journal of General Virology (2003), 84, 3453-3457.

A Comparison of the Lymphocyte Subpopulations of Pigs Experimentally Infected with Porcine Circovirus 2 and/or Parvovirus; Kim and Chae; The Veterinary Journal 2003, 165, 325-329.

Evaluation of a porcine circovirus type 2-specific antigen-capture enzyme-linked immunosorbent assay for the diagnosis of postweaning multisystemic wasting syndrome in pigs: comparison with virus isolation, immunohistochemistry, and the polyerase chain reaction; McNeilly, McNair, O'Connor, Brockbank, Gilpin, Lasagna, Boriosi, Meehan, Ellis, Krakowka, Allan; J Vet Diagn Invest 14:106-112 (2002).

The Effects of Immuno-modulation on the Clinical and Pathological Expression of Postweaning Multisystemic Wasting Syndrome; Kyriakis, Saoulidis, Lekkas, Miliotis, Papoutsis, Kennedy; J. Comp. Path. 2002, vol. 126, 38-46.

Development and application of a competitive enzyme-linked immunosorbent assay for the detection of serum antibodies to porcine circovirus type 2; Walker, Konoby, Jewhurst, McNair, McNeilly, Meehan, Cottrell, Ellis, Allan; J Vet Diagn Invest 12:400-405 (2000).

Development of a polyclonal-antibody-based immunohistochemical method for the detection of type 2 porcine circovirus in formalin-fixed, paraffin-embedded tissue; Sorden, Harms, Nawagitgul, Cavanaugh, Paul; J Vet Diagn Invest 11:528-530 (1999).

Molecular characterization of Porcine circovirus type 2 isolates from post-weaning multisystemic wasting syndrome-affected and non-affected pigs; Boisseson, Beven, Bigarre, Thiery, Rose, Eveno, Madec, Jestin; Journal of General Virology (2004), 85, 293-304.

An Experimental Model for Post-weaning Multisystemic Wasting Syndrome (PMSW) in Growing Piglets; Albina, Truong, Hutet, Blanchard, Cariolet, Hospitaller, Mahe, Allee, Morvan, Amenna, Dimna, Madec, Jestin; J Comp Path 2001, vol. 125, 292-303.

"Letters" The Veterinary Record, Aug. 5, 2000; p. 170-171.

Protection of swine against post-weaning multisystemic wasting syndrome (PMWS) by porcine circovirus type 2 (PCV2) proteins; Blanchard, Mahe, Cariolet, Keranflec'h, Baudouard, Cordioli, Albina, Jestin; Vaccine 21 (2003) 4565-4575.

Porcine circoviruses: a review; Allan, Ellis; J Vet Diagn Invest 12:3-14 (2000).

Postweaning multisystemic wasting syndrome (PMWS) in pigs. A review; Segales, Domingo; Veterinary Quarterly 2002; 24(3): 109-124.

Conjugated Linoleic Acid Ameliorates Viral Infectivity in a Pig Model of Virally Induced Immunosuppression; Bassaganya-Riera, Pogranichniy, Jobgen, Halbur, Yoon, O'Shea, Mohede, Hontecillas; Nutritional Immunology(2003) 3204-3214.

Epidemiology of porcine circovirus type 2 infection: what do we know?; Segales, Calsamiglia, Domingo; Pig News and Information, vol. 24 (2003) pgs. 103N-110N.

Use of a polymerase chain reaction assay and an ELISA to monitor porcine circovirus type 2 infection in pigs from farms with and without postweaning multisystemic wasting syndrome; Sibila, Calsamiglia, Segales, Blanchard, Badiella, LeDimna, Jestin, Domingo; AJVR, vol. 65, No. 1, Jan. 2004.

Dendritic Cells Harbor Infectious Porcine Circovirus Type 2 in the Absence of Apparent Cell Modulation or Replication of the Virus; Vincent, Carrasco, Herrmann, Meehan, Allan, Summerfield, McCullough; Journal of Virology, Dec. 2003, p. 13288-13300 (vol. 77, No. 24).

Kinetics of porcine circovirus type 2 replication; Cheung and Bolin; Archives of Virology (2002) 147:43-58.

Virus-Like Particle Production at Low Multiplicities of Infection With the Baculovirus Insect Cell System; Maranga, Brazao, Carrondo; Aug. 2003 Wiley InterScience (Wiley Periodicals) pp. 245-253.

Changes in peripheral blood leukocyte populations in pigs with natural postweaning multisystemic wasting syndrome (PMWS); Segales, Alonso, Rosell, Pastor, Chianini, Campos, Lopez-Fuertes, Qunitant, Rodriguez-Arrioja, Calsamiglia, Pujols, Dominguez, Domingo; Veterinary Immunology and Immunopathology 81 (2001) 37-44.

Experimental infection of colostrum deprived piglets with porcine circovirus 2 (PCV2) and porcine reproductive and respiratory syndrome virus (PRRSV) potentiates PCV2 replication; Allan, McNeilly, Ellis, Krakowka, Meehan, McNair, Walker, Kennedy; Archives of Virology (2000) 145: 2421-2429.

Experimental Inoculation of Conventional Pigs with Porcine Reproductive and Respiratory Syndrome Virus and Porcine Circovirus 2; Rovira, Balasch, Segales, Garcia, Plana-Duran, Rosell, Ellerbrok, Mankertz, Domingo; Journal of Virology, Apr. 2002, p. 3232-3239 (vol. 76, No. 7).

Reproduction of postweaning multisystemic wasting syndrome (PMWS) in immunostimulated and non-immunostimulated 3-week-old piglets experimentally infected with porcine circovirus type 2

(PCV2); Ladekjaer-Mikkelsen, Nielsen, Stadejek, Storgaard, Krakowka, Ellis, McNeilly, Allan, Botner, Veterinary Microbiology 89 (2002) 97-114.

Open reading frame 2 of porcine circovirus type 2 encodes a major capsid protein; Nawagitgul, Morozov, Bolin, Harms, Sorden, Paul; Jounal of General Virology (2000), 81, 2281-2287.

Postweaning multisystemic wasting syndrome: a review of aetiology, diagnosis and pathology; C. Chae; The Veterinary Journal 168 (2004) 41-49.

Ponsich, Etude Preliminaire De L'Impact Du Circovac Sur L'infection Par Le PCV2 En Maternite, Nov. 10, 1981.

Kixmoller, et al., Reduction of PMWS-associated clinical signs and co-infections by vaccination against PCV2, Vaccine 26 (2008) 3443-51.

Fachinger, et al., The effect of vaccination against porcine circovirus type 2 in pigs suffering from porcine respiratory disease complex, Vaccine (2008) 26, 1488-99.

Chiou, et al., The Effect of Porcine Circovirus Infection on the Immune Response of Pigs After Vaccination Against Classical Swine Fever and Pseudorabies, Proceedings of the 19th IPVS Congress. Copenhagen, Denmark, 2006, vol. 2.

Charbonneau, Canadian Experiences with Porcine Circovirus Associated Disease. Iowa Pork Congress, 2007.

Allan, et al., PMWS/PCVD: Diagnosis, Disease, and Control: What do we know?, Proceedings of the 19th IPVS Congress. Copenhagen, Denmark, 2006, vol I, 3-9.

Allan et al., Passive Transfer of Material Antibodies to PCV2 Protects Against Development of Post-weaning Multisystemic Wasting Syndrome (PMWS): Experimental Infections and a Field Study, The Pig Journal, 2002, 50, 59-67.

Kamstrup, et al., Immunisation against PCV2 structural protein by DNA vaccination of mice, Vaccine, 2004, 22, 1358-1361.

Kost, et al., Recombinant baculoviruses as mammalian cell gene delivery vectors, Trends in Biology, 2002, 20, 173-180.

Groener, The Biology of Baculoviruses, vol. 1, Biological Properties and Molecular Biology, Chapter 9, Specificity and Safety of Baculoviruses, 1986, 177-202.

* cited by examiner

METHODS OF OVEREXPRESSION AND RECOVERY OF PORCINE CIRCOVIRUS TYPE 2 ORF2

RELATED APPLICATIONS

This application claims the benefit of provisional application Ser. No. 60/640,510, now expired, filed on Dec. 30, 2004, the teachings and content of which are hereby incorporated by reference.

SEQUENCE LISTING

This application contains a sequence listing in paper format and in computer readable format, the teachings and content of which are hereby incorporated by reference.

BACKGROUND OF THE INVENTION

1. Field of the Invention

The present invention is concerned with the recovery of a protein expressed by open reading frame 2 of porcine circovirus type 2. More particularly, the protein is a recombinant protein expressed by a transfected virus containing recombinant coding sequences for porcine circovirus type 2, open reading frame 2. Still more particularly, the transfected virus is permitted to infect cells in growth media and the protein expressed by open reading frame 2 is recovered in the supernate, rather than from inside the cells. Even more particularly, the method involves the steps of amplifying the open reading frame 2 gene from porcine circovirus type 2, cloning this amplified portion into a first vector, excising the open reading frame 2 portion from this first vector and cloning it into a transfer vector, cotransfecting the transfer vector with a viral vector into cells in growth media, causing the cells to become infected by the viral vector and thereby express open reading frame 2, and recovering the expressed recombinant protein coded for by open reading frame 2 in the supernate.

2. Description of the Prior Art

Porcine circovirus type 2 (PCV2) is a small (17-22 nm in diameter), icosahedral, non-enveloped DNA virus, which contains a single-stranded circular genome. PCV2 shares approximately 80% sequence identity with procine circovirus type 1 (PCV1). However, in contrast with PCV1, which is generally non-virulent, swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In some affected swine, a combination of all symptoms will be apparent while other swine will only have one or two of these symptoms. During necropsy, microscopic and macroscopic lesions also appear on multiple tissues and organs with lymphoid organs being the most common site for lesions. A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia.

Open reading frame 2 (ORF2) protein of PCV2, having an approximate molecular weight of 30 kDa when run on SDS-PAGE gel, has been utilized in the past as an antigenic component in vaccines for PCV2. Typical methods of obtaining ORF2 for use in such vaccines generally consist of amplifying the PCV2 DNA coding for ORF2, transfecting a viral vector with the ORF2 DNA, infecting cells with the viral vector containing the ORF2 DNA, permitting the virus to express ORF2 protein within the cell, and extracting the ORF2 protein from the cell via cell lysis. These procedures generally take up to about four days after infection of the cells by the viral vector. However, these procedures suffer because the extraction procedures are both costly and time-consuming. Additionally, the amount of ORF2 recovered from the cells is not very high; consequently, a large number of cells need to be infected by a large number of viral vectors in order to obtain sufficient quantities of the recombinant expressed protein for use in vaccines and the like. Accordingly, what is needed in the art is a method of obtaining ORF2 protein which does not require extraction of the ORF2 protein from within infected cells. What is further needed are methods of obtaining recombinant ORF2 protein sufficient for efficiently preparing vaccine compositions. Finally, what is needed are methods of obtaining ORF2 protein which do not require the complicated and labor-intensive methods required by the current ORF2 protein extraction protocols.

SUMMARY OF THE INVENTION

The present invention overcomes the problems inherent in the prior art and provides a distinct advance in the state of the art. Specifically, the present invention provides improved methods of recovering recombinant PCV2 ORF2 protein, by permitting infection of susceptible cells in culture with a recombinant viral vector containing ORF2 DNA coding sequences, wherein ORF2 protein is expressed by the recombinant virus, and recovering the ORF2 in the supernate. It has been unexpectedly discovered that ORF2 is released into the supernate in large quantities if the infection and subsequent incubation of the infected cells is allowed to progress past the typical ORF2 recovery process which extracts the ORF2 from within cells. Preferred cell cultures have a cell count between about $0.3$-$2.0 \times 10^6$ cells/mL, more preferably from about $0.35$-$1.9 \times 10^6$ cells/mL, still more preferably from about $0.4$-$1.8 \times 10^6$ cells/mL, even more preferably from about $0.45$-$1.7 \times 10^6$ cells/mL, and most preferably from about $0.5$-$1.5 \times 10^6$ cells/mL. Preferred cells are determinable by those of skill in the art. Preferably the cells are insect cells, and more preferably, they include the Sf+ insect cells (Protein Sciences Corporation, Meridan, Conn.). Appropriate growth media will also be determinable by those of skill in the art with a preferred growth media being serum-free insect cell media such as Excell 420 (JRH Biosciences, Inc., Lenexa, Kans.). The recombinant viral vector containing the PCV2 ORF2 DNA sequences has a preferred multiplicity of infection (MOI) of between about 0.03-1.5, more preferably from about 0.05-1.3, still more preferably from about 0.09-1.1, and most preferably from about 0.1-1.0. Preferred viral vectors include baculovirus such as BaculoGold (BD Biosciences Pharmingen, San Diego, Calif.). Although the baculovirus expression system is preferred, it is understood by those of skill in the art that other expression systems will work for purposes of the present invention, namely the expression of PCV2 ORF2 into the supernatant of a cell culture. Such other expression systems may require the use of a signal sequence in order to cause ORF2 expression into the media. It has been discovered that when ORF2 is produced by a baculovirus expression system, this protein can independently form virus-like particles and is recognized by hyperimmune rabbit serum. Moreover, the baculovirus expression system does not require any signal sequence or further modification to cause expression of ORF2 into the media. The infected cells are then incubated over a period of up to ten days, more preferably from about two days to about ten days, still more preferably from about four days to about nine days, and most preferably from about five days to about eight days. Preferred incubation conditions include a temperature between about 22-32° C., more preferably from about 24-30° C., still more preferably from about 25-29° C., even more preferably from about 26-28° C., and most preferably about 27° C. Preferably, the Sf+ cells are observed following inoculation for characteristic baculovirus-induced changes. Such observation may include monitoring cell density trends and the decrease in viability during the post-infection period. It was found that peak viral titer is observed 3-5 days after infection and peak ORF2 release from the cells into the supernate is obtained between days 5 and 8 when cell viability decreases to less than 10%. Additionally, it is preferred that the culture be periodically examined for macroscopic and microscopic evidence of contamination or for atypical changes in cell morphology during the post-infection period. Any culture exhibiting any contamination should be discarded. Preferably, the expressed ORF2 recombinant protein is secreted by the cells into the surrounding growth media that maintains cell viability. The ORF2 is then recovered in the supernate surrounding the cells rather than from the cells themselves.

The recovery process preferably begins with the separation of cell debris from the expressed ORF2 in media via a separation step. Preferred separation steps include filtration, centrifugation at speeds up to about 20,000×g, continuous flow centrifugation, chromatographic separation using ion exchange or gel filtration, and conventional immunoaffinity methods. The most preferred separation methods include centrifugation at speeds up to about 20,000×g and filtration. Preferred filtration methods include dead-end microfiltration and tangential flow (or cross flow) filtration including hollow fiber filtration dead-end micro filtration. Of these, dead-end microfiltration is preferred. Preferred pore sizes for dead-end microfiltration are between about 0.30-1.35 µm, more preferably between about 0.35-1.25 µm, still more preferably between about 0.40-1.10 µm, and most preferably between about 0.45-1.0 µm. It is believed that any conventional filtration membrane will work for purposes of the present invention and polyethersulfone membranes are preferred. Any low weight nucleic acid species are removed during the filtration step.

For recovery of PCV2 ORF2 that will be used in vaccines, the inclusion of an inactivation step is preferred in order to inactivate the viral vector. Preferably, this inactivation is done either just before or just after the filtration step, with after the filtration step being the preferred time for inactivation. In preferred forms, the volume of harvest fluids is determined and the temperature is brought to between about 32-42° C., more preferably between about 34-40° C., and most preferably between about 35-39° C. Any conventional inactivation method can be used for purposes of the present invention. Preferred inactivation methods include the addition of a 0.4M solution of 2-bromoethyleneamine hydrobromide, which has been cyclized to 0.2M binary ethylenimine (BEI) in 0.3N NaOH, to the fluids to give a final concentration of about 5 mM BEI. The fluids are then stirred continuously for 72-96 hours and the inactivated harvest fluids can be stored frozen at −40° C. or below or between about 1-7° C. A 1.0M sodium thiosulfate solution to give a final minimum concentration of 5 mM is added to neutralize any residual BEI.

In preferred forms and especially in forms that will use the recombinant PCV2 ORF2 protein in vaccines, each lot of harvested ORF2 will be tested for inactivation by passage in the anchorage dependent, baculovirus susceptible Sf9 cells. In a preferred form of this testing, 150 $cm^2$ of appropriate cell culture monolayer is inoculated with 1.0 mL of inactivated PCV2 fluids and maintained at 25-29° C. for 14 days with at least two passages. At the end of the maintenance period, the cell monolayers are examined for CPE typical of PCV2 ORF2 baculovirus. Preferably, positive virus controls are also used. Such controls can consist of one culture of Sf9 cells inoculated with a reference PCV2 ORF2 baculovirus and one flask of Sf9 cells that remain uninoculated. After incubation and passage, the absence of virus-infected cells in the BEI treated viral fluids would constitute a satisfactory inactivation test. The control cells inoculated with the reference virus should exhibit CPE typical of PCV2 ORF2 baculovirus and the uninoculated flask should not exhibit any evidence of PCV2 ORF2 baculovirus CPE. Alternatively, at the end of the maintenance period, the supernatant samples could be collected and inoculated onto a Sf9 96 well plate, which was maintained at 25-29° C. for 5-6 days. The plate is then fixed and stained with anti-PCV2 ORF2 antibody conjugated to FITC. The absence of CPE and ORF2 expression, as detected by IFA microscopy, in the BEI treated viral fluids constitutes a satisfactory inactivation test. The control cells inoculated with the reference virus should exhibit CPE and IFA activity and the uninoculated flask should not exhibit any evidence of PCV2 ORF2 baculovirus CPE and contain no IFA activity.

After inactivation, the relative amount of recombinant ORF2 protein in a sample can be determined in a number of ways. Preferred methods of quantitation include SDS-PAGE densitometry, ELISA, and animal vaccination studies that correlate known quantities of vaccine with clinical outcomes (serology, etc.). When SDS-PAGE is utilized for quantitation, the sample material containing an unknown amount of recombinant ORF2 protein is run on a gel, together with samples that contain different known amounts of recombinant ORF2 protein. A standard curve can then be produced based on the known samples and the amount of recombinant ORF2 in the unknown sample can be determined by comparison with this standard curve. Because ELISAs are generally recognized as the industry standard for antigen quantitation, they are preferred for quantitation. A preferred ELISA will generally begin with diluting the capture antibody 1:6000 or an appropriate working dilution in coating buffer. A preferred capture antibody is Swine anti-PCV2 PAb Prot. G purified and a preferred coating buffer is 0.05M Carbonate buffer, which can be made by combining 2.93 g $NaHCO_3$ (Sigma Cat. No. S-6014, or equivalent) and 1.59 g $NaCO_3$ (Sigma Cat. No. S-6139, or equivalent). The mixture is combined with distilled water, or equivalent, to make one liter at a ph of 9.6±0.1. Next, the capture antibody is diluted 1:6,000, or any other appropriate working dilution, in coating buffer. For example, for four plates, one would need 42 mLs of coating buffer and seven μL of capture antibody. Using a reverse pipetting method, 100 μL of diluted capture antibody is added to all of the wells. In order to obtain an even coating, the sides of each plate should be gently tapped. The plates are then sealed with plate sealers, prior to stacking the plates and capping the stack with an empty 96-well plate. The plates are incubated overnight (14-24 hours) at 35-39° C. Each plate is then washed three times with wash buffer using the ultra wash plus micro titer plate washer set at 250 μL/wash with three washes and 0 soak time. After the last wash the plates should be tapped onto a paper towel. Again using the reverse pipetting technique, 250 μL of blocking solution should be added to all of the wells. The test plates should be sealed and incubated for approximately one hour (±five minutes) at 35-37° C. Preferably, the plates will not be stacked after this step. During the blocking step, all test samples should be pulled out and thawed at room temperature. Next, four separate dilution plates should be prepared by adding 200 μL of diluent solution to all of the remaining wells except for row A and row H, columns 1-3. Next, six test tubes should be labeled as follows, low titer, medium titer, high titer, inactivated/filtered (1:240), inactivated/filtered (1:480), and internal control. In the designated tubes, an appropriate dilution should be prepared for the following test samples. The thawed test samples should be vortexed prior to use. For four plates, the following dilutions will be made: A) the low titer will not be pre-diluted: 3.0 mLs of low titer; B) negative control at a 1:30 dilution (SF+ cells): 3.77 mLs of diluent+130 μL of the negative control; C) medium titer at a 1:30 dilution (8 μg/mL): 3.77 mLs of diluent+130 μL of the medium titer; D) high titer at a 1:90 dilution (16 μg/mL): 2.967 mLs of diluent+33 μL of high titer; E) inactivated/filtered at a 1:240 dilution: 2.39 mLs of diluent+10 μL of inactivated/filtered sample; F) inactivated/filtered at a 1:480 dilution: 1.0 mL of diluent+1.0 mL of inact/filtered (1:240) prepared sample from E above; G) internal control at 1:30 dilution: 3.77 mLs of diluent+130 μL of the internal control. Next, add 300 μL of the prepared samples to corresponding empty wells in the dilution plates for plates 1 through 4. The multichannel pipettor is then set to 100 μL, and the contents in Row A are mixed by pipetting up and down for at least 5 times and then 100 μL is transferred to Row B using the reverse pipetting technique. The tips should be changed and this same procedure is followed down the plate to Row G. Samples in these dilution plates are now ready for transfer to the test plates once the test plates have been washed 3 times with wash buffer using the ultrawash plus microtiter plate washer (settings at 250 μL/wash, 3 washes, 0 soak time). After the last wash, the plates should be tapped onto a paper towel. Next, the contents of the dilution plate are transferred to the test plate using a simple transfer procedure. More specifically, starting at row H, 100 μL/well is transferred from the dilution plate(s) to corresponding wells of the test plate(s) using reverse pipetting technique. After each transfer, the pipette tips should be changed. From Row G, 100 μL/well in the dilution plate(s) is transferred to corresponding wells of the test plate(s) using reverse pipetting technique. The same set of pipette tips can be used for the remaining transfer. To ensure a homogenous solution for the transfer, the solution should be pipetted up and down at least 3 times prior to transfer. Next, the test plate(s) are sealed and incubated for 1.0 hour±5 minutes at 37 20 C.±2.0° C. Again, it is preferable to not stack the plates. The plates are then washed 3 times with wash buffer using the ultrawash plus microtiter plate washer (settings at 250 μL/wash, 3 washes, and 0 soak time). After the last wash, the plates are tapped onto a paper towel. Using reverse pipetting technique, 100 μL of detection antibody diluted 1:300, or appropriate working dilution, in diluent solution is added to all of the wells of the test plate(s). For example, for four plates, one will need 42 mLs of diluent solution with 140 μL of capture antibody. The test plate(s) are then sealed and incubated for 1.0 hour±5 minutes at 37° C.±2.0° C. Again, the plates are washed 3 times with wash buffer using the ultrawash plus microtiter plate washer (settings at 250 μL/wash, 3 washes, and 0 soak time). After the last wash, the plates are tapped onto a paper towel. Next, the conjugate diluent is prepared by adding 1% normal rabbit serum to the diluent. For example, for four plates, 420 μL of normal rabbit serum is added to 42 mL of diluent. The conjugate antibody is diluted to 1:10,000, or any other appropriate working dilution, in a freshly prepared conjugate diluent solution to all wells of the test plate(s). Using a reverse pipetting technique, 100 μL of this diluted conjugate antibody is added to all the wells. The test plate(s) are then sealed and incubated for 45±5 minutes at 37° C.±2.0° C. Preferably, the plates are not stacked. The plates are then washed 3 times with wash buffer using the ultrawash plus microtiter plate washer (settings at 250 μL/wash, 3 washes, and 0 soak time). After the last wash, the plates are tapped onto a paper towel. Next, equal volumes of TMB Peroxidase Substrate (Reagent A) with Peroxidase Solution B (Reagent B) are mixed immediately prior to use. The amount mixed will vary depending upon the quantity of plates but each plate will require 10 mL/plate+2 mLs. Therefore, for 4 plates, it will be 21 mL of Reagent A+21 mL of Reagent B. Using a reverse pipetting technique, 100 μL of substrate is added to all wells of the test plate(s). The plates are then incubated at room temperature for 15 minutes±15 seconds. The reaction is stopped by the addition of 100 μL of 1N HCl solution to all wells using a reverse pipetting technique. The ELISA plate reader is then turned on and allowed to proceed through its diagnostics and testing phases in a conventional manner.

In preferred forms, the recombinant viral vector used to infect the cells is transfected from a transfer vector that has had the ORF2 gene cloned therein. One preferred transfer vector is the pVL1392 vector (BD Biosciences Pharmingen), which is designed for co-transfection with the BaculoGold DNA into the preferred Sf9 cell line. The construct co-transfected is approximately 10,387 base pairs in length.

In more preferred forms, the method of the present invention will begin with the isolation of PCV2 ORF2 DNA. Generally, this can be from a known or unknown strain as the ORF2 DNA appears to be highly conserved with at least about 95% sequence identity between different isolates. Any PCV2 ORF2 gene can be used for purposes of the present invention as each would be expressed into the supernate. The ORF2 DNA is then amplified using PCR methods, together with the introduction of a 5'Kozak's consensus sequence (CCGCCAUG) (SEQ ID NO 1) and a 3'EcoR1 site (GAATTC) (SEQ ID NO 2). The amplified ORF2 gene, with these additional sequences, is cloned into a vector. A preferred vector for this initial cloning step is the pGEM-T-Easy Vector (Promega, Madison, Wis.). The ORF2 gene including some pGEM vector sequences (SEQ ID NO: 7) is excised from the vector at the NotI restriction site. It is this gene that is then cloned into the transfer vector.

In one aspect of the present invention a method of recovering recombinant protein expressed by open reading frame 2 of PCV2 is provided. The method generally comprises the steps of:

A) cloning a recombinant PCV2 open reading frame 2 from PCV2 into a transfer vector;
B) transfecting the portion of the transfer vector containing the recombinant open reading frame 2 into a virus;
C) infecting cells in media with the transfected virus;
D) causing the transfected virus to express the recombinant protein from PCV2 open reading frame 2;
E) separating cells from the supernate; and
F) recovering the expressed open reading frame 2 protein in the supernate.

Optionally, this method can include the step of amplifying the PCV2 open reading frame 2 from a strain of PCV2 prior to cloning the open reading frame into the transfer vector. In preferred forms, a 5'Kozak's sequence, a 3' EcoR1 site, and combinations thereof can also be added to the amplified sequence, preferably prior to amplification. A preferred 5'Kozak's sequence comprises SEQ ID No: 1. A preferred 3' EcoR1 site comprises SEQ ID No: 2. Preferred PCV2 open reading frame 2 nucleotide sequences comprise Genbank Accession No. AF086834 (SEQ ID NO: 3) and SEQ ID NO:

4. Preferred recombinant PCV2 recombinant proteins comprise SEQ ID NO: 5, which is the protein encoded by SEQ ID NO: 3 (Genbank Accession No. AF086834) and SEQ ID No: 6, which is the protein encoded by SEQ ID NO: 4. A preferred media comprises serum-free insect cell media, still more preferably Excell 420 media. When the optional amplification step is performed, it is preferable to first clone the amplified open reading frame 2 into a first vector, excise the open reading frame 2 from the first vector, and use the excised open reading frame for cloning into the transfer vector. A preferred cell line for cotransfection is the SF+cell line. A preferred virus is for cotransfection is baculovirus. In preferred forms of this method, the transfected portion comprises SEQ ID No: 8. Finally, for this method, it is preferred to recover the PCV2 open reading frame 2 protein in the cell culture supernate at least 5 days after infecting the cells with the virus.

In another aspect of the present invention, a method for preparing a composition for invoking an immune response against PCV2 is provided. Generally, this method includes the steps of transfecting a construct into a virus, wherein the construct comprises recombinant DNA from open reading frame 2 of PCV2, infecting cells in growth media with the transfected virus, causing the virus to express the recombinant protein from PCV2 open reading frame 2, recovering the expressed open reading frame 2 protein in the supernate, and preparing the composition by combining the recovered protein with a suitable adjuvant. In preferred forms of this method, the construct is obtained in a transfer vector. Optionally, the method may include the step of amplifying the open reading frame 2 from a strain of PCV2 through PCR prior to cloning the open reading frame 2 into the transfer vector. Preferred open reading frame sequences, Kozak's sequences, 3' EcoR1 site sequences, recombinant protein sequences, transfected construct sequences, media, cells, and viruses are as described in the previous methods. Another optional step for this method includes cloning the amplified PCV2 open reading frame 2 into a first vector, excising the open reading frame 2 from this first vector, and using this excised PCV2 open reading frame 2 for cloning into the transfer vector. As with the other methods, it is preferred to wait for at least 5 days after infection of the cells by the transfected baculovirus prior to recovering recombinant ORF2 protein in the supernate. Preferably, the recovery step of this method also includes the step of separating the media from the cells and cell debris. This can be done in a variety of ways but for ease and convenience, it is preferred to filter the cells, cell debris, and growth media through a filter having pores ranging in size from about 0.45 µM to about 1.0 µM. Finally, for this method, it is preferred to include an virus inactivation step prior to combining the recovered recombinant PCV2 ORF2 protein in a composition. This can be done in a variety of ways but it is preferred to use BEI.

In another aspect of the present invention, an improved method of recovering the protein expressed by open reading frame 2 from PCV2 is provided. This method generally includes the steps of infecting cells in growth media with a recombinant viral vector containing PCPV2 open reading frame 2 DNA coding sequences, and causing the vector to express the recombinant ORF2 protein. However, this method is distinct from the prior art methods in that the next step recovers the expressed recombinant protein in the supernate, rather than by treating the cells or requiring additional steps to recover expressed ORF2 protein from the cells. In practicing this method, those of skill in the art will understand that the preferred materials and optional steps described above for other methods of the invention are equally applicable to this method

DETAILED DESCRIPTION OF THE PREFERRED EMBODIMENTS

The following examples set forth preferred materials and procedures in accordance with the present invention. It is to be understood, however, that these examples are provided by way of illustration only, and nothing therein should be deemed a limitation upon the overall scope of the invention.

Example 1

This example compares the relative yields of ORF2 using methods of the present invention and methods of the prior art. Four 1000 mL spinner flasks were each seeded with approximately $1.0 \times 10^6$ Sf+ cells/ml in 300 mL of insect serum free media, Excell 420 (JRH Biosciences, Inc., Lenexa, Kans.). The master cell culture is identified as SF+ (*Spodoptera frugiperda*) Master Cell Stock, passage 19, Lot#N112-095W. The cells used to generate the SF+Master Cell Stock were obtained from Protein Sciences Corporation, Inc., Meriden, Conn. The SF+ cell line for this example was confined between passages 19 and 59. Other passages will work for purposes of the present invention but in order to scale the process up for large scale production, at least 19 passages will probably be necessary and passages beyond 59 my have an effect on expression, although this was not investigated. In more detail, the initial SF+ cell cultures from liquid nitrogen storage were grown in Excell 420 media in suspension in sterile spinner flasks with constant agitation. The cultures were grown in 100 mL to 250 mL spinner flasks with 25 to 150 mL of Excell 420 serum-free media. When the cells had multiplied to a cell density of $1.0-8.0 \times 10^6$ cells/mL, they were split to new vessels with a planting density of $0.5-1.5 \times 10^6$ cells/mL. Subsequent expansion cultures were grown in spinner flasks up to 36 liters in size or in stainless steel bioreactors of up to 300 liters for a period of 2-7 days at 25-29° C.

Figure 1:
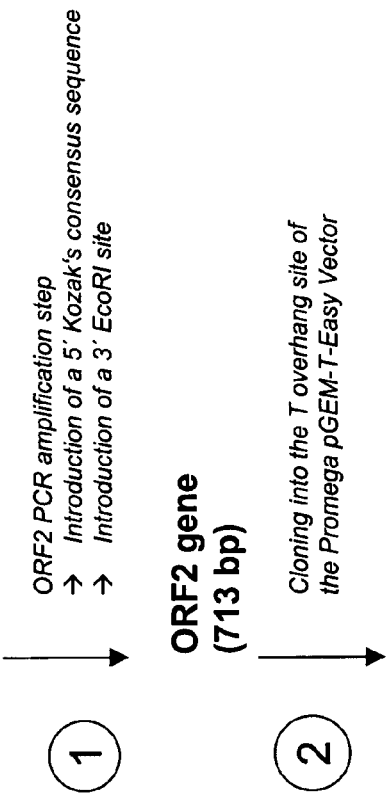
FIG. 1 is a schematic flow diagram of a preferred construction of PCV2 ORF2 recombinant baculovirus.
Figure 1:
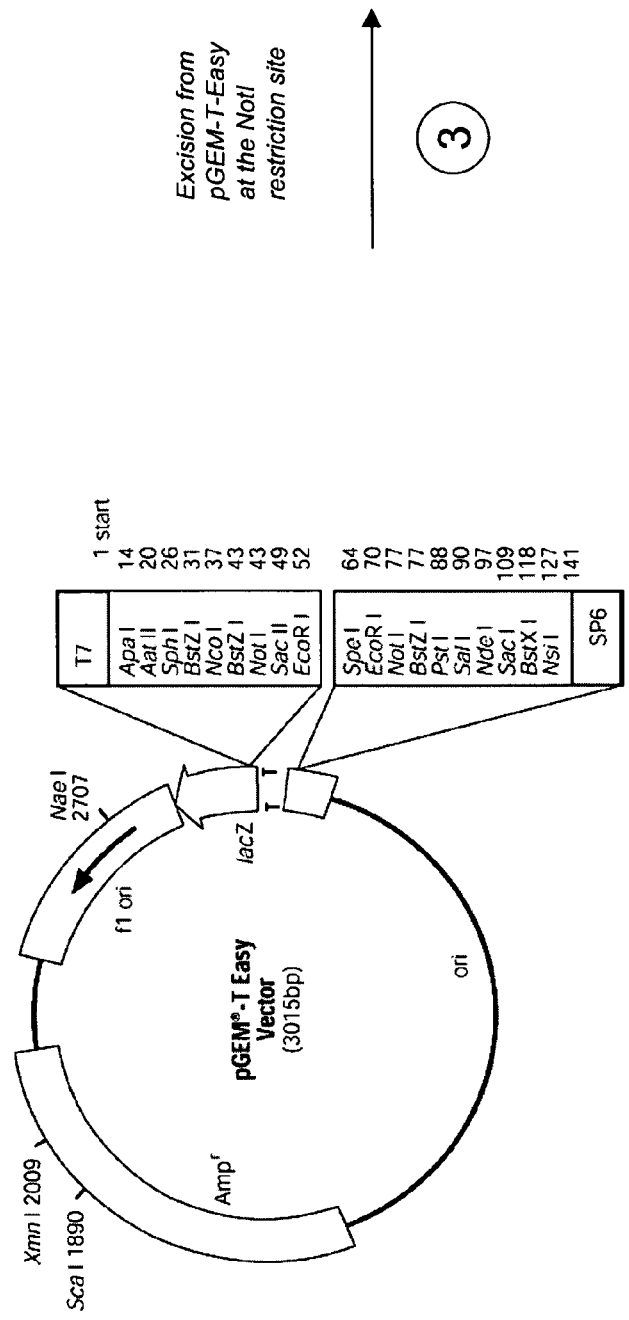
Figure 1:
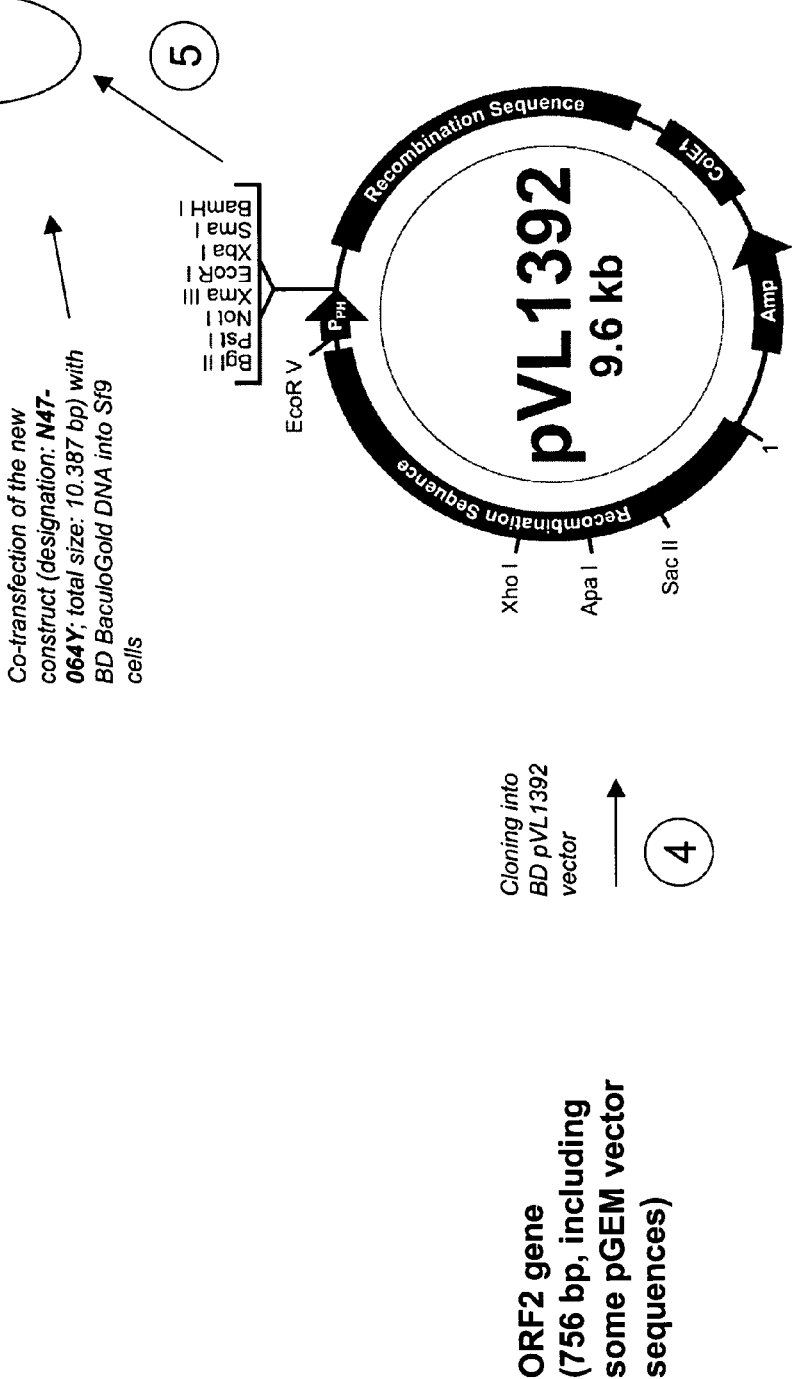

After seeding, the flasks were incubated at 27° C. for four hours. Subsequently, each flask was seeded with a recombinant baculovirus containing the PCV2 ORF2 gene (SEQ ID NO: 4). The recombinant baculovirus containing the PCV2 ORF2 gene was generated as follows: the PCV2 ORF2 gene from a North American strain of PCV2 was PCR amplified to contain a 5'Kozak's sequence (SEQ ID NO: 1) and a 3' EcoR1 site (SEQ ID NO: 2), cloned into the pGEM-T-Easy vector (Promega, Madison, Wis.), and was subsequently excised and subcloned into the transfer vector pVL1392 (BD Biosciences Pharmingen, San Diego, Calif.). The subcloned portion is represented herein as SEQ ID NO: 7. The pVL1392 plasmid containing the PCV2 ORF2 gene was designated N47-064Y and then co-transfected with BaculoGold® (BD Biosciences Pharmingen) baculovirus DNA into Sf9 insect cells (Protein Sciences, Meriden, Conn.) to generate the recombinant baculovirus containing the PCV2 ORF2 gene. The new construct is provided herein as SEQ ID NO: 8. The recombinant baculovirus containing the PCV2 ORF2 gene was plaque-purified and Master Seed Virus (MSV) was propagated on the SF+ cell line, aliquoted, and stored at −70° C. The MSV was positively identified as PCV2 ORF2 baculovirus by PCR-RFLP using baculovirus specific primers. Insect cells infected with PCV2 ORF2 baculovirus to generate MSV or Working Seed Virus express PCV2 ORF2 antigen as detected by polyclonal serum or monoclonal antibodies in an indirect fluorescent antibody assay. Additionally, the identity of the PCV2 ORF2 baculovirus was confirmed by N-terminal amino acid sequencing. The PCV2 ORF2 baculovirus MSV was also tested for purity in accordance with 9 C.F.R. 113.27 (c), 113.28, and 113.55. Each recombinant baculovirus seeded into the spinner flasks had varying multiplicities of infection (MOIs). Flask 1 was seeded with 7.52 mL of 0.088 MOI seed; flask 2 was seeded with 3.01 mL of 0.36 MOI seed; flask 3 was seeded with 1.5 mL of 0.18 MOI seed; and flask 4 was seeded with 0.75 mL of 0.09 MOI seed. A schematic flow diagram illustrating the basic steps used to construct a PCV2 ORF2 recombinant baculovirus is provided herein as FIG. 1.

After being seeded with the baculovirus, the flasks were then incubated at 27±2° C. for 7 days and agitated at 100 rpm during that time. The flasks used ventilated caps to allow for air flow. Samples from each flask were taken every 24 hours for the next 7 days. After extraction, each sample was centrifuged, and both the pellet and the supernatant were separated and then microfiltered through a 0.45-1.0 μm pore size membrane.

The resulting samples then had the amount of ORF2 present within them quantified via an ELISA assay. The ELISA assay was conducted with capture antibody Swine anti-PCV2 Pab IgG Prot. G purified (diluted 1:250 in PBS) diluted to 1:6000 in 0.05M Carbonate buffer (pH 9.6). 100 μL of the antibody was then placed in the wells of the microtiter plate, sealed, and incubated overnight at 37° C. The plate was then washed three times with a wash solution (0.5 mL of Tween 20 (Sigma, St. Louis, Mo.), 100 mL of 10×D-PBS (Gibco Invitrogen, Carlsbad, Calif.) and 899.5 mL of distilled water. Subsequently, 250 μL of a blocking solution (5 g Carnation Non-fat dry milk (Nestle, Glendale, Calif.) in 10 mL of D-PBS QS to 100 mL with distilled water) was added to each of the wells. The next step was to wash the test plate and then add pre-diluted antigen. The pre-diluted antigen was produced by adding 200 μL of diluent solution (0.5 mL Tween 20 in 999.5 mL D-PBS) to each of the wells on a dilution plate. The sample was then diluted at a 1:240 ration and a 1:480 ratio and 100 μL of each of these diluted samples was then added to one of the top wells on the dilution plate (i.e. one top well received 100 μL of the 1:240 dilution and the other received 100 μL of the 1:480 dilution. Serial dilutions were then done for the remainder of the plate by removing 100 μL form each successive well and transferring it to the next well on the plate. Each well was mixed prior to doing the next transfer. The test plate washing included washing the plate three times with the wash buffer. The plate was then sealed and incubated for an hour at 37° C. before being washed three more times with the wash buffer. The detection antibody used was monoclonal antibody to PCV ORF2. It was diluted to 1:300 in diluent solution, and 100 μL of the diluted detection antibody was then added to the wells. The plate was then sealed and incubated for an hour at 37° C. before being washed three times with the wash buffer. Conjugate diluent was then prepared by adding normal rabbit serum (Jackson Immunoresearch, West Grove, Pa.) to the diluent solution to 1% concentration. Conjugate antibody Goat anti-mouse (H+1)-HRP (Jackson Immunoresearch) was diluted in the conjugate diluent to 1:10,000. 100 μL of the diluted conjugate antibody was then added to each of the wells. The plate was then sealed and incubated for 45 minutes at 37° C. before being washed three times with the wash buffer. 100 μL of substrate (TMB Peroxidase Substrate, Kirkgaard and Perry Laboratories (KPL), Gaithersberg, Md.), mixed with an equal volume of Peroxidase Substrate B (KPL) was added to each of the wells. The plate was incubated at room temperature for 15 minutes. 100 μL of 1N HCL solution was then added to all of the wells to stop the reaction. The plate was then run through an ELISA reader. The results of this assay are provided in Table 1 below:

TABLE 1

| Day | Flask | ORF2 in pellet (μg) | ORF2 in supernatant (μg) |
|---|---|---|---|
| 3 | 1 | 47.53 | 12 |
| 3 | 2 | 57.46 | 22 |
| 3 | 3 | 53.44 | 14 |
| 3 | 4 | 58.64 | 12 |
| 4 | 1 | 43.01 | 44 |
| 4 | 2 | 65.61 | 62 |
| 4 | 3 | 70.56 | 32 |
| 4 | 4 | 64.97 | 24 |
| 5 | 1 | 31.74 | 100 |
| 5 | 2 | 34.93 | 142 |
| 5 | 3 | 47.84 | 90 |
| 5 | 4 | 55.14 | 86 |
| 6 | 1 | 14.7 | 158 |
| 6 | 2 | 18.13 | 182 |
| 6 | 3 | 34.78 | 140 |
| 6 | 4 | 36.88 | 146 |
| 7 | 1 | 6.54 | 176 |
| 7 | 2 | 12.09 | 190 |
| 7 | 3 | 15.84 | 158 |
| 7 | 4 | 15.19 | 152 |

These results indicate that when the incubation time is extended, expression of ORF2 into the supernatant of the centrifuged cells and media is greater than expression in the pellet of the centrifuged cells and media. Accordingly, allowing the ORF2 expression to proceed for at least 5 days and recovering it in the supernate rather than allowing expression to proceed for less than days and recovering ORF2 from the cells, appears to provide a great increase in ORF2 yields.

Example 2

This example provides data as to the efficacy of the invention claimed herein. A 1000 mL spinner flask was seeded with approximately $1.0\times10^6$Sf+ cells/ml in 300 mL of Excell 420 media. The flask was then incubated at 27° C. and agitated at 100 rpm. Subsequently, the flask was seeded with 10 mL of PCV2 ORF2/Bac p+6 (the recombinant baculovirus containing the PCV2 ORF2 gene passaged 6 additional times in the Sf9 insect cells) virus seed with a 0.1 MOI after 24 hours of incubation.

The flask was then incubated at 27° C. for a total of 6 days. After incubation, the flask was then centrifuged and three samples of the resulting supernatant were harvested and inactivated. The supernatant was inactivated by bringing its temperature to 37±2° C. To the first sample, a 0.4M solution of 2-bromoethyleneamine hydrobromide which had been cyclized to 0.2M binary ethylenimine (BET) in 0.3N NaOH is added to the supernatant to give a final concentration of BEI of 5 mM. To the second sample, 10 mM BEI was added to the supernatant. To the third sample, no BEI was added to the supernatant. The samples were then stirred continuously for 48 hrs. A 1.0 M sodium thiosulfate solution to give a final minimum concentration of 5 mM was added to neutralize any residual BEI. The quantity of ORF2 in each sample was then quantified using the same ELISA assay procedure as described in Example 1. The results of this may be seen in Table 2 below:

TABLE 2

| Sample | ORF2 in supernatant (μg) |
|---|---|
| 1 | 78.71 |
| 2 | 68.75 |
| 3 | 83.33 |

This example demonstrates that neutralization with BEI does not remove or degrade significant amounts of the recombinant PCV2 ORF2 protein product. This is evidenced by the fact that there is no large loss of ORF2 in the supernatant from the BEI or elevated temperatures. Those of skill in the art will recognize that the recovered ORF2 is a stable protein product.

Example 3

This example demonstrates that the present invention is scalable from small scale production of recombinant PCV2 ORF2 to large scale production of recombinant PCV2 ORF2. $5.0 \times 10^5$ cells/ml of SF+ cells/ml in 7000 mL of ExCell 420 media was planted in a 20000 mL Applikon Bioreactor. The media and cells were then incubated at 27° C. and agitated at 100 RPM for the next 68 hours. At the $68^{th}$ hour, 41.3 mL of PCV2 ORF2 Baculovirus MSV+3 was added to 7000 mL of ExCell 420 medium. The resultant mixture was then added to the bioreactor. For the next seven days, the mixture was incubated at 27° C. and agitated at 100 RPM. Samples from the bioreactor were extracted every 24 hours beginning at day 4, post-infection, and each sample was centrifuged. The supernatant of the samples were preserved and the amount of ORF2 was then quantified using SDS-PAGE densitometry. The results of this can be seen in Table 3 below:

TABLE 3

| Day after infection: | ORF2 in supernatant (μg/mL) |
|---|---|
| 4 | 29.33 |
| 5 | 41.33 |
| 6 | 31.33 |
| 7 | 60.67 |

We claim:

1. A method of recovering recombinant protein expressed by open reading frame 2 of PCV2 comprising the steps of:
   i) infecting insect cells in culture with a recombinant baculovirus vector containing and expressing said open reading frame 2 protein of PCV2, and
   ii) recovering at least 41.33 μg/ml of said expressed open reading frame 2 protein of PCV2 from the supernate after infecting said cells with the recombinant baculovirus.

2. The method of claim 1, wherein said expressed open reading frame 2 protein of PCV2 is recovered from the supernate at least 5 days after the said insect cells are infected with the recombinant baculovirus containing and expressing said open reading frame 2 protein of PCV2.

3. The method of claim 1, wherein said open reading frame 2 of PCV2 comprises the sequence of SEQ ID No: 4.

4. The method of claim 1, wherein said recombinant expressed open reading frame 2 protein of PCV2 comprises the sequence of SEQ ID No: 6.

5. The method of claim 1, wherein said culture comprises serum-free insect cell media.

6. The method of claim 1, further comprising the step of mixing said recovered open reading frame 2 protein of PCV2 with an adjuvant.

7. The method of claim 6, wherein the method further includes the step of inactivating the baculovirus prior to combining said recovered open reading frame 2 protein of PCV-2 with a suitable adjuvant.

8. The method of claim 1, further comprising the steps of:
   i. cloning the open reading frame 2 of PCV2 into a first vector;
   ii. excising the open reading frame 2 of PCV2 from said first vector; and
   iii. cloning the excised open reading frame 2 of PCV2 into a baculovirus.

9. A method of recovering recombinant protein expressed by open reading frame 2 of PCV2 comprising the steps of:
   i) infecting insect cells in culture with a recombinant baculovirus vector containing and expressing said open reading frame 2 protein of PCV2;
   ii) separating said insect cells and insect cell debris from the expressed open reading frame 2 protein; and
   iii) recovering at least 41.33 μg/ml of said expressed open reading frame 2 protein of PCV2 from the supernate.

10. The method of claim 9, wherein said separation is done by a filtration step.

11. The method of claim 10, wherein said filtration step includes the step of filtering said culture through a filter having pores ranging in size from about 0.45 μM to about 1.0 μM.

12. The method of claim 9, wherein said expressed open reading frame 2 protein of PCV2 is recovered from the supernate at least 5 days after said insect cells are infected with the recombinant baculovirus containing and expressing said open reading frame 2 protein of PCV2.

13. The method of claim 9, wherein said open reading frame 2 of PCV2 comprises the sequence of SEQ ID No: 4.

14. The method of claim 9, wherein said recombinant expressed open reading frame 2 protein of PCV2 comprises the sequence of SEQ ID No: 6.

15. The method of claim 9, wherein said culture is serum-free insect cell medium.

16. The method of claim 9, further comprising the step of mixing said recovered open reading frame 2 protein of PCV2 with an adjuvant.

17. The method of claim 16, wherein the method further includes the step of inactivating the baculovirus prior to combining said recovered open reading frame 2 protein of PCV2 with a suitable adjuvant.

18. The method of claim 9, further comprising the steps of:
   i. cloning the open reading frame 2 of PCV2 into a first vector;
   ii. excising the open reading frame 2 of PCV2 from said first vector; and
   iii. cloning the excised open reading frame 2 of PCV2 into a baculovirus.

* * * * *

```
                      SEQUENCE LISTING

<160> NUMBER OF SEQ ID NOS: 8

<210> SEQ ID NO 1
<211> LENGTH: 8
<212> TYPE: DNA
<213> ORGANISM: Artificial
<220> FEATURE:
<223> OTHER INFORMATION: This is a modified Kozak's sequence

<400> SEQUENCE: 1 ccgccatg                                                                8

<210> SEQ ID NO 2
<211> LENGTH: 6
<212> TYPE: DNA
<213> ORGANISM: Artificial
<220> FEATURE:
<223> OTHER INFORMATION: This is a recombinant Eco R1 sequence.

<400> SEQUENCE: 2 gaattc                                                                  6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc      60
ttggccagat cctccgccgc cgcccctggc tcgtccaccc ccgccaccgc taccgttgga    120
gaaggaaaaa tggcatcttc aacacccgcc tctcccgcac cttcggatat actgtggaga    180
aggaaaaatg gcatcttcaa cacccgcctc tcccgcacct tcggatatac tgtggagact    240
ttgttccccc gggagggggg accaacaaaa tctctatacc ctttgaatac tacagaataa    300
gaaaggttaa ggttgaattc tggccctgct cccccatcac ccagggtgat aggggagtgg    360
gctccactgc tgttattcta gatgataact ttgtaacaaa ggccacagcc ctaacctatg    420
acccatatgt aaactactcc tcccgccata caatccccca acccttctcc taccactccc    480
```

```
gttacttcac acccaaacct gttcttgact ccactattga ttacttccaa ccaaataaca    540
aaaggaatca gctttggctg aggctacaaa cctctagaaa tgtggaccac gtaggcctcg    600
gcactgcgtt cgaaaacagt aaatacgacc aggactacaa tatccgtgta accatgtatg    660
tacaattcag agaatttaat cttaaagacc ccccacttaa accctaaatg aat            713

<210> SEQ ID NO 4
<211> LENGTH: 713
<212> TYPE: DNA
<213> ORGANISM: Porcine circovirus

<400> SEQUENCE: 4
ccgccatgac gtatccaagg aggcgttacc gcagaagaag acaccgcccc cgcagccatc     60
ttggccagat cctccgccgc cgcccctggc tcgtccaccc ccgccaccgc taccgttgga    120
gaaggaaaaa tggcatcttc aacacccgcc tctcccgcac cttcggatat actgtcaagg    180
ctaccacagt cacaacgccc tcctgggcgg tggacatgat gagatttaat attgacgact    240 tgttccccc gggaggggggg accaacaaaa tctctatacc ctttgaatac tacagaataa    300
gaaaggttaa ggttgaattc tggccctgct cccccatcac ccagggtgat aggggagtgg    360
gctccactgc tgttattcta gatgataact ttgtaacaaa ggccacagcc ctaacctatg    420
acccatatgt aaactactcc tcccgccata caatccccca accttctcc taccactccc     480 gttacttcac acccaaacct gttcttgact ccactattga ttacttccaa ccaaataaca    540
aaaggaatca gctttggctg aggctacaaa cctctagaaa tgtggaccac gtaggcctcg    600
gcactgcgtt cgaaaacagt aaatacgacc aggactacaa tatccgtgta accatgtatg    660
tacaattcag agaatttaat cttaaagacc ccccacttga accctaagaa ttc            713

<210> SEQ ID NO 5
<211> LENGTH: 233
<212> TYPE: PRT
<213> ORGANISM: Porcine circovirus

<400> SEQUENCE: 5

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160
```

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
                180                 185                 190

Val Asp His Val Gly Leu Gly Thr Ala Phe Glu Asn Ser Lys Tyr Asp
                195                 200                 205

Gln Asp Tyr Asn Ile Arg Val Thr Met Tyr Val Gln Phe Arg Glu Phe
            210                 215                 220

Asn Leu Lys Asp Pro Pro Leu Lys Pro
225             230

<210> SEQ ID NO 6
<211> LENGTH: 233
<212> TYPE: PRT
<213> ORGANISM: Porcine circovirus

<400> SEQUENCE: 6

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
                35                  40                  45

Leu Ser Arg Thr Phe Gly Tyr Thr Val Lys Ala Thr Thr Val Thr Thr
            50                  55                  60

Pro Ser Trp Ala Val Asp Met Met Arg Phe Asn Ile Asp Asp Phe Val
65              70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
            130                 135                 140

Ser Ser Arg His Thr Ile Pro Gln Pro Phe Ser Tyr His Ser Arg Tyr
145             150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
                180                 185                 190

Val Asp His Val Gly Leu Gly Thr Ala Phe Glu Asn Ser Lys Tyr Asp
                195                 200                 205

Gln Asp Tyr Asn Ile Arg Val Thr Met Tyr Val Gln Phe Arg Glu Phe
            210                 215                 220

Asn Leu Lys Asp Pro Pro Leu Glu Pro
225             230

<210> SEQ ID NO 7
<211> LENGTH: 756
<212> TYPE: DNA
<213> ORGANISM: Artificial
<220> FEATURE:
<223> OTHER INFORMATION: This sequence is from porcine circovirus type
      2, open reading frame 2, together with a portion from the pGEM
      T-easy vector.

<400> SEQUENCE: 7

-continued gcggccgcgg gaattcgatc cgccatgacg tatccaagga ggcgttaccg cagaagaaga 60
caccgccccc gcagccatct tggccagatc ctccgccgcc gcccctggct cgtccacccc 120
cgccaccgct accgttggag aaggaaaaat ggcatcttca acacccgcct ctcccgcacc 180
ttcggatata ctgtcaaggc taccacagtc acaacgccct cctgggcggt ggacatgatg 240
agatttaata ttgacgactt tgttcccccg ggagggggga ccaacaaaat ctctataccc 300
tttgaatact acagaataag aaaggttaag gttgaattct ggccctgctc ccccatcacc 360
cagggtgata ggggagtggg ctccactgct gttattctag atgataactt tgtaacaaag 420
gccacagccc taacctatga cccatatgta aactactcct cccgccatac aatcccccaa 480
cccttctcct accactcccg ttacttcaca cccaaacctg ttcttgactc cactattgat 540
tacttccaac caaataacaa aaggaatcag ctttggctga ggctacaaac ctctagaaat 600
gtggaccacg taggcctcgg cactgcgttc gaaaacagta aatacgacca ggactacaat 660
atccgtgtaa ccatgtatgt acaattcaga gaatttaatc ttaaagaccc ccccacttgaa 720 ccctaagaat tctatcacta gtgaattcgc ggccgc 756

<210> SEQ ID NO 8
<211> LENGTH: 10387
<212> TYPE: DNA
<213> ORGANISM: Artificial
<220> FEATURE:
<223> OTHER INFORMATION: This is the porcine circovirus type 2, ORF2 construct, which includes baculovirus and pGEM T-easy coding sequences.

<400> SEQUENCE: 8
aagctttact cgtaaagcga gttgaaggat catatttagt tgcgtttatg agataagatt 60
gaaagcacgt gtaaaatgtt tcccgcgcgt tggcacaact atttacaatg cggccaagtt 120
ataaaagatt ctaatctgat atgttttaaa acacctttgc ggcccgagtt gtttgcgtac 180
gtgactagcg aagaagatgt gtggaccgca gaacagatag taaaacaaaa ccctagtatt 240
ggagcaataa tcgatttaac caacacgtct aaatattatg atggtgtgca ttttttgcgg 300
gcgggcctgt tatacaaaaa aattcaagta cctggccaga ctttgccgcc tgaaagcata 360
gttcaagaat ttattgacac ggtaaaagaa tttacagaaa agtgtcccgg catgttggtg 420
ggcgtgcact gcacacacgg tattaatcgc accggttaca tggtgtgcag atatttaatg 480
cacaccctgg gtattgcgcc gcaggaagcc atagatagat tcgaaaaagc cagaggtcac 540
aaaattgaaa gacaaaatta cgttcaagat ttattaattt aattaatatt atttgcattc 600
tttaacaaat actttatcct attttcaaat tgttgcgctt cttccagcga accaaaacta 660
tgcttcgctt gctccgttta gcttgtagcc gatcagtggc gttgttccaa tcgacggtag 720
gattaggccg gatattctcc accacaatgt tggcaacgtt gatgttacgt ttatgctttt 780
ggttttccac gtacgtcttt tggccggtaa tagccgtaaa cgtagtgccg tcgcgcgtca 840
cgcacaacac cggatgtttg cgcttgtccg cggggtattg aaccgcgcga tccgacaaat 900
ccaccacttt ggcaactaaa tcggtgacct gcgcgtcttt ttctgcatt atttcgtctt 960 tcttttgcat ggtttcctgg aagccggtgt acatgcggtt tagatcagtc atgacgcgcg 1020
tgacctgcaa atctttggcc tcgatctgct tgtccttgat ggcaacgatg cgttcaataa 1080
actcttgttt tttaacaagt tcctcggttt tttgcgccac caccgcttgc agcgcgtttg 1140
tgtgctcggt gaatgtcgca atcagcttag tcaccaactg tttgctctcc tcctcccgtt 1200

```
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca acatcgcaa aagccaatag   1800
tacagttttg atttgcatat taacggcgat ttttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gttttttacga agcgatgaca   2520
tgaccccgt agtgacaacg atcacgccca aaagaactgc cgactacaaa attaccgagt   2580
atgtcggtga cgttaaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga agaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatcttta   3180
atcaaatccc aagatgtgta taaccacca aactgccaaa aatgaaaac tgtcgacaag   3240
ctctgtccgt ttgctggcaa ctgcaagggt ctcaatccta tttgtaatta ttgaataata   3300
aaacaattat aaatgctaaa tttgtttttt attaacgata caaaccaaac gcaacaagaa   3360
catttgtagt attatctata attgaaaacg cgtagtata atcgctgagg taatatttaa   3420
aatcattttc aaatgattca cagttaattt gcgacaatat aattttattt tcacataaac   3480
tagacgcctt gtcgtcttct tcttcgtatt ccttctcttt ttcattttc tcctcataaa   3540
aattaacata gttattatcg tatccatata tgtatctatc gtatagagta aatttttgt   3600
```

```
tgtcataaat atatatgtct tttttaatgg ggtgtatagt accgctgcgc atagtttttc    3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat tttttagcag caccggatta acataacttt    3840
ccaaaatgtt gtacgaaccg ttaaacaaaa acagttcacc tccctttcct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc gggaattcga tccgccatga cgtatccaag gaggcgttac cgcagaagaa    4200
gacaccgccc ccgcagccat cttggccaga tcctccgccg ccgcccctgg ctcgtccacc    4260
cccgccaccg ctaccgttgg agaaggaaaa atggcatctt caacacccgc tctcccgca    4320 ccttcggata tactgtcaag gctaccacag tcacaacgcc ctcctgggcg gtggacatga    4380
tgagatttaa tattgacgac tttgttcccc cgggagggg gaccaacaaa atctctatac    4440
cctttgaata ctacagaata agaaaggtta aggttgaatt ctggccctgc tcccccatca    4500
cccagggtga taggggagtg ggctccactg ctgttattct agatgataac tttgtaacaa    4560
aggccacagc cctaacctat gacccatatg taaactactc ctcccgccat acaatccccc    4620 aaccttctc ctaccactcc cgttacttca cacccaaacc tgttcttgac tccactattg    4680
attacttcca accaaataac aaaaggaatc agctttggct gaggctacaa acctctagaa    4740
atgtggacca cgtaggcctc ggcactgcgt tcgaaaacag taaatacgac caggactaca    4800
atatccgtgt aaccatgtat gtacaattca gagaatttaa tcttaaagac cccccacttg    4860
aaccctaaga attctatcac tagtgaattc gcggccgccg ccgctccag aattctagaa    4920 ggtacccggg atcctttcct gggacccggc aagaaccaaa aactcactct cttcaaggaa    4980
atccgtaatg ttaaacccga cacgatgaag cttgtcgttg gatggaaagg aaaagagttc    5040
tacagggaaa cttggacccg cttcatggaa gacagcttcc ccattgttaa cgaccaagaa    5100
gtgatggatg ttttccttgt tgtcaacatg cgtcccacta gacccaaccg ttgttacaaa    5160
ttcctggccc aacacgctct gcgttgcgac cccgactatg tacctcatga cgtgattagg    5220
atcgtcgagc cttcatgggt gggcagcaac aacgagtacc gcatcagcct ggctaagaag    5280
ggcggcggct gcccaataat gaaccttcac tctgagtaca ccaactcgtt cgaacagttc    5340
atcgatcgtg tcatctggga gaacttctac aagcccatcg tttacatcgg taccgactct    5400
gctgaagagg aggaaattct ccttgaagtt tccctggtgt tcaaagtaaa ggagtttgca    5460
ccagacgcac ctctgttcac tggtccggcg tattaaaaca cgatacattg ttattagtac    5520
atttattaag cgctagattc tgtgcgttgt tgatttacag acaattgttg tacgtatttt    5580 ataattcat taaatttata atctttaggg tggtatgtta gagcgaaaat caaatgattt    5640
tcagcgtctt tatatctgaa tttaaatatt aaatcctcaa tagatttgta aaataggttt    5700
cgattagttt caaacaaggg ttgttttttcc gaaccgatgg ctggactatc taatggattt    5760
tcgctcaacg ccacaaaact tgccaaatct tgtagcagca atctagcttt gtcgatattc    5820
gtttgtgttt tgttttgtaa taaaggttcg acgtcgttca aaatattatg cgcttttgta    5880
tttctttcat cactgtcgtt agtgtacaat tgactcgacg taaacacgtt aaataaagct    5940
```

```
tggacatatt taacatcggg cgtgttagct ttattaggcc gattatcgtc gtcgtcccaa    6000
ccctcgtcgt tagaagttgc ttccgaagac gattttgcca tagccacacg acgcctatta    6060
attgtgtcgg ctaacacgtc cgcgatcaaa tttgtagttg agcttttttgg aattatttct   6120 gattgcgggc gttttttgggc gggtttcaat ctaactgtgc ccgattttaa ttcagacaac   6180
acgttagaaa gcgatggtgc aggcggtggt aacatttcag acggcaaatc tactaatggc   6240
ggcggtggtg gagctgatga taaatctacc atcggtggag gcgcaggcgg ggctggcggc   6300
ggaggcggag gcggaggtgg tggcggtgat gcagacggcg gtttaggctc aaatgtctct   6360
ttaggcaaca cagtcggcac ctcaactatt gtactggttt cgggcgccgt ttttggtttg   6420
accggtctga gacgagtgcg attttttttcg tttctaatag cttccaacaa ttgttgtctg   6480
tcgtctaaag gtgcagcggg ttgaggttcc gtcggcattg gtggagcggg cggcaattca   6540
gacatcgatg gtggtggtgg tggtggaggc gctggaatgt taggcacggg agaaggtggt   6600
ggcggcggtg ccgccggtat aatttgttct ggtttagttt gttcgcgcac gattgtgggc   6660
accggcgcag gcgccgctgg ctgcacaacg gaaggtcgtc tgcttcgagg cagcgcttgg   6720
ggtggtggca attcaatatt ataattggaa tacaaatcgt aaaaatctgc tataagcatt   6780
gtaatttcgc tatcgtttac cgtgccgata tttaacaacc gctcaatgta agcaattgta   6840
ttgtaaagag attgtctcaa gctcgccgca cgccgataac aagccttttc atttttacta   6900
cagcattgta gtggcgagac acttcgctgt cgtcgacgta catgtatgct ttgttgtcaa   6960
aaacgtcgtt ggcaagcttt aaaatattta aaagaacatc tctgttcagc accactgtgt   7020
tgtcgtaaat gttgtttttg ataatttgcg cttccgcagt atcgacacgt tcaaaaaatt   7080
gatgcgcatc aattttgttg ttcctattat tgaataaata agattgtaca gattcatatc   7140
tacgattcgt catggccacc acaaatgcta cgctgcaaac gctggtacaa ttttacgaaa   7200
actgcaaaaa cgtcaaaact cggtataaaa taatcaacgg gcgctttggc aaaatatcta   7260
ttttatcgca caagcccact agcaaattgt atttgcagaa aacaatttcg gcgcacaatt   7320
ttaacgctga cgaaataaaa gttcaccagt taatgagcga ccacccaaat tttataaaaa   7380
tctattttaa tcacggttcc atcaacaacc aagtgatcgt gatggactac attgactgtc   7440
ccgatttatt tgaaacacta caaattaaag gcgagctttc gtaccaactt gttagcaata   7500
ttattagaca gctgtgtgaa gcgctcaacg atttgcacaa gcacaatttc atacacaacg   7560
acataaaact cgaaaatgtc ttatatttcg aagcacttga tcgcgtgtat gtttgcgatt   7620
acggattgtg caaacacgaa aactcactta gcgtgcacga cggcacgttg gagtattta    7680 gtccggaaaa aattcgacac acaactatgc acgtttcgtt tgactggtac gcggcgtgtt   7740
aacatacaag ttgctaacgt aatcatggtc atagctgttt cctgtgtgaa attgttatcc   7800
gctcacaatt ccacacaaca tacgagccgg aagcataaag tgtaaagcct ggggtgccta   7860
atgagtgagc taactcacat taattgcgtt gcgctcactg cccgctttcc agtcgggaaa   7920
cctgtcgtgc cagctgcatt aatgaatcgg ccaacgcgcg gggagaggcg gtttgcgtat   7980
tgggcgctct tccgcttcct cgctcactga ctcgctgcgc tcggtcgttc ggctgcggcg   8040
agcggtatca gctcactcaa aggcggtaat acggttatcc acagaatcag gggataacgc   8100
aggaaagaac atgtgagcaa aaggccagca aaaggccagg aaccgtaaaa aggccgcgtt   8160
gctggcgttt ttccataggc tccgcccccc tgacgagcat cacaaaaatc gacgctcaag   8220
tcagaggtgg cgaaacccga caggactata aagataccag gcgtttcccc ctggaagctc   8280
cctcgtgcgc tctcctgttc cgaccctgcc gcttaccgga tacctgtccg cctttctccc   8340
```

```
ttcgggaagc gtggcgcttt ctcatagctc acgctgtagg tatctcagtt cggtgtaggt   8400
cgttcgctcc aagctgggct gtgtgcacga accccccgtt cagcccgacc gctgcgcctt   8460
atccggtaac tatcgtcttg agtccaaccc ggtaagacac gacttatcgc cactggcagc   8520
agccactggt aacaggatta gcagagcgag gtatgtaggc ggtgctacag agttcttgaa   8580
gtggtggcct aactacggct acactagaag gacagtattt ggtatctgcg ctctgctgaa   8640
gccagttacc ttcggaaaaa gagttggtag ctcttgatcc ggcaaacaaa ccaccgctgg   8700
tagcggtggt ttttttgttt gcaagcagca gattacgcgc agaaaaaaag gatctcaaga   8760
agatcctttg atcttttcta cggggtctga cgctcagtgg aacgaaaact cacgttaagg   8820
gattttggtc atgagattat caaaaaggat cttcacctag atccttttaa attaaaaatg   8880
aagtttttaaa tcaatctaaa gtatatatga gtaaacttgg tctgacagtt accaatgctt   8940
aatcagtgag gcacctatct cagcgatctg tctatttcgt tcatccatag ttgcctgact   9000
ccccgtcgtg tagataacta cgatacggga gggcttacca tctggcccca gtgctgcaat   9060
gataccgcga gacccacgct caccggctcc agatttatca gcaataaacc agccagccgg   9120
aagggccgag cgcagaagtg gtcctgcaac tttatccgcc tccatccagt ctattaattg   9180
ttgccgggaa gctagagtaa gtagttcgcc agttaatagt ttgcgcaacg ttgttgccat   9240
tgctacaggc atcgtggtgt cacgctcgtc gtttggtatg gcttcattca gctccggttc   9300
ccaacgatca aggcgagtta catgatcccc catgttgtgc aaaaaagcgg ttagctcctt   9360
cggtcctccg atcgttgtca gaagtaagtt ggccgcagtg ttatcactca tggttatggc   9420
agcactgcat aattctctta ctgtcatgcc atccgtaaga tgcttttctg tgactggtga   9480
gtactcaacc aagtcattct gagaatagtg tatgcggcga ccgagttgct cttgcccggc   9540
gtcaatacgg gataataccg cgccacatag cagaacttta aaagtgctca tcattggaaa   9600
acgttcttcg gggcgaaaac tctcaaggat cttaccgctg ttgagatcca gttcgatgta   9660
acccactcgt gcacccaact gatcttcagc atcttttact ttcaccagcg tttctgggtg   9720
agcaaaaaca ggaaggcaaa atgccgcaaa aaagggaata agggcgacac ggaaatgttg   9780
aatactcata ctcttccttt ttcaatatta ttgaagcatt tatcagggtt attgtctcat   9840
gagcggatac atatttgaat gtatttagaa aaataaacaa ataggggttc cgcgcacatt   9900
tccccgaaaa gtgccacctg acgtctaaga accattatt atcatgacat taacctataa   9960
aaataggcgt atcacgaggc cctttcgtct cgcgcgtttc ggtgatgacg gtgaaaacct  10020
ctgacacatg cagctcccgg agacggtcac agcttgtctg taagcggatg ccgggagcag  10080
acaagcccgt cagggcgcgt cagcgggtgt tggcgggtgt cggggctggc ttaactatgc  10140
ggcatcagag cagattgtac tgagagtgca ccatatgcgg tgtgaaatac cgcacagatg  10200
cgtaaggaga aaataccgca tcaggcgcca ttcgccattc aggctgcgca actgttggga  10260
agggcgatcg gtgcgggcct cttcgctatt acgccagctg gcgaaagggg gatgtgctgc  10320
aaggcgatta agttgggtaa cgccagggtt ttcccagtca cgacgttgta aaacgacggc  10380
cagtgcc                                                           10387
```